(12) United States Patent
Sekido et al.

(10) Patent No.: US 6,503,223 B1
(45) Date of Patent: Jan. 7, 2003

(54) BALLOON CATHETER

(75) Inventors: Akira Sekido, Tokyo (JP); Masaru Uchiyama, Kanagawa (JP); Shinichi Miyata, Tokyo (JP); Takashi Kawabata, Saitama (JP)

(73) Assignee: Nippon Zeon Co., Ltd., Tokyo (JP)

( * ) Notice: Subject to any disclaimer, the term of this patent is extended or adjusted under 35 U.S.C. 154(b) by 0 days.

(21) Appl. No.: 09/646,396

(22) PCT Filed: Mar. 18, 1999

(86) PCT No.: PCT/JP99/01347

§ 371 (c)(1),
(2), (4) Date: Sep. 18, 2000

(87) PCT Pub. No.: WO99/47203

PCT Pub. Date: Sep. 23, 1999

(30) Foreign Application Priority Data

Mar. 18, 1998 (JP) .......................................... 10-089306

(51) Int. Cl.$^7$ ............................................. A61M 29/00
(52) U.S. Cl. .................... 604/96.01; 604/264; 604/535; 606/192; 606/194
(58) Field of Search .............................. 604/96.01, 264, 604/523, 535; 606/192, 194

(56) References Cited

U.S. PATENT DOCUMENTS

| | | | | | |
|---|---|---|---|---|---|
| 5,300,025 | A | * | 4/1994 | Wantink ................... | 604/96.01 |
| 5,649,909 | A | * | 7/1997 | Cornelius ................ | 604/96.01 |
| 5,743,875 | A | * | 4/1998 | Sirhan et al. ............ | 604/96.01 |
| 5,797,877 | A | * | 8/1998 | Hamilton et al. ........ | 604/96.01 |
| 5,807,355 | A | * | 9/1998 | Ramzipoor et al. ......... | 604/282 |
| 5,833,706 | A | * | 11/1998 | Germain et al. ......... | 604/96.01 |
| 6,238,376 | B1 | * | 5/2001 | Peterson ..................... | 604/264 |
| 6,273,899 | B1 | * | 8/2001 | Kramer ................... | 604/96.01 |

FOREIGN PATENT DOCUMENTS

| | | | |
|---|---|---|---|
| JP | 1-21064 | * | 5/1989 |
| JP | 5-137793 | * | 6/1993 |
| WO | 92/03178 | * | 3/1992 |
| WO | 94/02197 | * | 2/1994 |
| WO | 96/33763 | * | 10/1996 |

* cited by examiner

Primary Examiner—Ronald Capossela
(74) Attorney, Agent, or Firm—Armstrong, Westerman & Hattori, LLP

(57) ABSTRACT

A balloon catheter provided with a first tubular member in which at least one balloon lumen is formed inside along a longitudinal direction thereof; a balloon unit which is communicated internally with the balloon lumen formed in the first tubular member and capable of being expanded by a fluid fed through that balloon lumen; a second tubular member extending axially inside the balloon unit and provided axially therein with at least one guidewire lumen; a distal end of the balloon unit connected with a distal end of said second tubular member; an overlapped portion formed by overlapping a proximal end of said second tubular member with a distal end of said first tubular member axially over a predetermined distance; a neck portion of a proximal end side of said balloon unit directly or indirectly connected with at least part of said overlapped portion so as to cover at least part of said overlapped portion; and a recess in which a part of an outer circumference of the proximal end of the second tubular member is received and which is formed axially on an outer circumference of the distal end of said first tubular member.

21 Claims, 10 Drawing Sheets

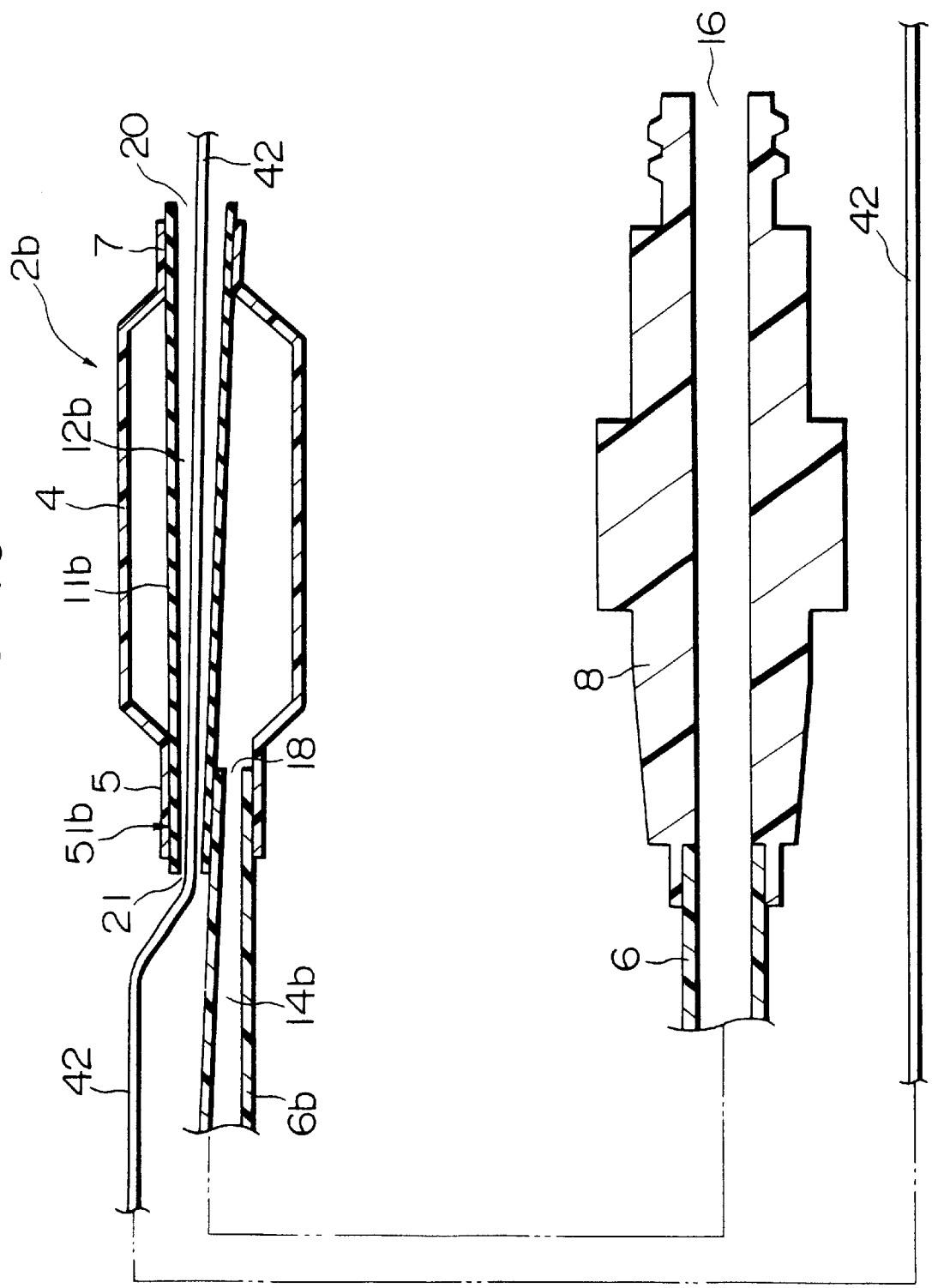

BALLOON CATHETER

TECHNICAL FIELD

The present invention relates to a balloon catheter suitably used as for example a balloon catheter for dilatation of blood vessels, more particularly relates to an improvement of a balloon catheter of a so-called monorail type.

BACKGROUND ART

In recent years, the trend in medical technology has been toward less invasive treatment. For example, stenosis of the coronary artery is increasingly being treated by vasodilation balloon catheters instead of the former coronary bypass surgery. This method of treatment has both economic advantages and lightens the load on the patient, so is increasingly growing in application. Along with this, balloon catheters are being required to be structured to enable dilatation of stenosis portions of the coronary artery more efficiently and simply than ever before.

As a method for treating stenosis portions in blood vessels, percutaneous transluminal coronary angioplasty (PTCA) is known. In this method, a balloon catheter is inserted into a blood vessel and the balloon unit is inflated so as to dilate the stenosis portion and thereby improve the flow of blood at the terminal side of the stenosis portion. As a balloon catheter used for this PTCA, there are an over-the-wire type balloon catheter and monorail type balloon catheter. In these types of balloon catheters, first the guidewire is made to pass through the stenosis portion in the blood vessel, then the balloon catheter is fed along the guidewire to the stenosis portion and the balloon unit inflated to dilate the stenosis portion. The stenosis portion must be dilated in stages so as not to damage the blood vessel. First, a balloon catheter with a small outside diameter balloon unit is inserted along the guidewire and then is exchanged with balloon catheters having successively larger outside diameter balloon units.

The over-the-wire type balloon catheter has a guidewire lumen formed over the entire length of the catheter tube. The guidewire is inserted along the lumen. The balloon unit is guided to the stenosis portion along this guidewire. After the dilatation of a blood vessel by a balloon catheter having a small outside diameter balloon unit, this is exchanged with a balloon catheter having a larger outside diameter balloon unit. At this time, the balloon catheter is pulled out along the guidewire, so the proximal end of the guidewire has to extend outside the body by at least the entire length of the catheter tube. If not, it is not possible to exchange a balloon catheter while leaving the distal end of the guidewire in the stenosis portion.

As opposed to this, in the monorail type balloon catheters disclosed in Japanese Unexamined Patent Publication (Kokai) No. 63-288167, U.S. Pat. No. 4,762,129, U.S. Pat. No. 5,061,273, or Japanese Unexamined Patent Publication (Kokai) No. 9-276411, an opening is formed in the middle of the catheter tube and a guidewire is guided from the opening through a guidewire insertion lumen to the distal end of the balloon unit. Due to this, in this type of balloon catheter, the length of the guidewire extending outside of the body for exchange of balloon catheters need only be slightly longer than the length from the opening to the distal end of the balloon. In this type, since the length of the guidewire can be shortened compared with the other type, the operability is excellent.

In the balloon catheters disclosed in the above publications, however, compared with the over-the-wire type, there was the problem of difficulty of insertion of the catheter into the blood vessel. As a method for dealing with this problem, a catheter tube where the distal end and proximal end of the catheter tube are comprised using different materials with different hardnesses and modulii of elasticity and these are joined to give a distal end with flexibility and a proximal end with rigidity has been reported. In this structure of a catheter tube, however, since the hardness changes sharply at the joined portion of the different materials, it is difficult to say that the operability is ideal. Further, since it is difficult to finish the joined portion completely smoothly, the catheter becomes difficult to insert into the blood vessel.

In the balloon catheter disclosed in U.S. Pat. No. 4,762,129, a dilatation use tubular member formed with a balloon inflation lumen and a wire use tubular member formed with a guidewire insertion lumen overlap over a predetermined distance along the axial direction. At the overlapped portion, the proximal end neck portion of the balloon unit is joined to cover part of the overlapped portion. In the balloon catheter disclosed in this publication, however, the outside diameter of the dilatation use tubular member becomes remarkably thinner compared with the portion overlapping the wire use tubular member, so there is the problem that kinks tend to occur.

Further, in the balloon catheter disclosed in U.S. Pat. No. 5,061,273, the dilatation use tubular member formed with the balloon inflation lumen and the wire use tubular member formed with the guidewire insertion lumen are overlapped across a predetermined distance along the axial direction at a position closer to the proximal end side than the proximal end of the balloon unit. Therefore, the outside diameter of the overlapped portion becomes larger and there is difficulty in the insertability of the balloon catheter. If the outside diameter of the dilatation use tubular member closer to the proximal end side than the overlapped portion is made smaller so as to reduce the outside diameter of the overlapped portion, there is also the problem that kinks tend to occur. Further, it is not possible to improve the strength of the proximal end neck portion of the balloon unit.

Further, in the balloon unit disclosed in Japanese Unexamined Patent Publication (Kokai) No. 9-276411, the ends of the two tubular members comprising the catheter tube are covered by separate tubular members, the outside diameters of those portions have thick step portions and there is difficulty in the insertability of the balloon catheter.

Further, in the technology disclosed in this publication, it is not possible to improve the strength of the proximal end neck portion of the balloon unit.

DISCLOSURE OF THE INVENTION

The present invention was made in consideration of this actual situation and has as its object the provision of a balloon catheter which is superior in insertability of the balloon catheter, improves the strength of the proximal end neck portion of the balloon unit, and is superior in resisting kinking.

To achieve the above object, the balloon catheter of the present invention comprises a first tubular member in which at least one balloon lumen is formed inside along a longitudinal direction thereof;

a balloon unit which is communicated internally with the balloon lumen formed in the first tubular member and capable of being expanded by a fluid fed through that balloon lumen; and a second tubular member extending axially inside the balloon unit and provided axially therein with at least one guidewire lumen;

a distal end of the balloon unit connected with a distal end of the second tubular member;

an overlapped portion formed by overlapping a proximal end of said second tubular member with a distal end of said first tubular member axially over a predetermined distance;

a neck portion of a proximal end side of said balloon unit directly or indirectly connected with at least part of said overlapped portion so as to cover at least part of said overlapped portion; and a portion of an outside diameter smaller than an outside diameter of a proximal end of the first tubular member, which is formed on the distal end of said first tubular member.

That is, the balloon c at hater of the present invention has as its object to keep the increase of the outside diameter of the overlapped portion the minimum necessary, to prevent the outside diameter of that portion from becoming thicker in sharp increments, and to improve the insertability of the balloon catheter in a blood vessel etc. and is characterized by having a portion with an outside diameter smaller than the outside diameter of a proximal end of the first tubular member, which is formed on the distal end of the first tubular member.

The balloon catheter according to a first aspect of the present invention comprises a first tubular member in which at least one balloon lumen is formed inside along a longitudinal direction thereof;

a balloon unit which is communicated internally with the balloon lumen formed in the first tubular member and capable of being expanded by a fluid fed through that balloon lumen;

a second tubular member extending axially inside the balloon unit and provided axially therein with at least one guidewire lumen;

a distal end of the balloon unit connected with a distal end of said second tubular member;

an overlapped portion formed by overlapping a proximal end of said second tubular member with a distal end of said first tubular member axially over a predetermined distance;

a neck portion of a proximal end side of said balloon unit directly or indirectly connected with at least part of said overlapped portion so as to cover at least part of said overlapped portion; and a recess in which a part of an outer circumference of the proximal end of the second tubular member is received and which is formed axially on an outer circumference of the distal end of said first tubular member.

A balloon catheter according to a second aspect of the present invention comprises a first tubular member in which at least one balloon lumen is formed inside along a longitudinal direction thereof;

a balloon unit which is communicated internally with the balloon lumen formed in the first tubular member and capable of being expanded by a fluid fed through that balloon lumen; and a second tubular member extending axially inside the balloon unit and provided axially therein with at least one guidewire lumen;

a distal end of the balloon unit connected with a distal end of said second tubular member;

an overlapped portion formed by overlapping a proximal end of said second tubular member with a distal end of said first tubular member axially over a predetermined distance;

a neck portion of a proximal end side of said balloon unit directly or indirectly connected with at least part of said overlapped portion so as to cover at least part of said overlapped portion; and a tapered portion where the outside diameter becomes smaller toward the distal end of the first tubular member, which is formed on at least a part of said first tubular member.

The second tubular member preferably has at least partially a tapered portion where the outside diameter becomes smaller toward the proximal end of the second tubular member.

The length of the overlapped portion is not particularly limited, but preferably is 2 mm to 500 mm. If the length of the overlapped portion is too short, the strength of the joined portion of the tubular members tends to become insufficient, while if too long, the material is wasted.

The axial length of the proximal end neck portion of the balloon unit may be longer or shorter than the axial length of the overlapped portion, but is preferably longer. If the neck portion is too long, however, the material is wasted, so the length is preferably not more than 500 mm. The reason why the neck portion is preferably longer than the length of the overlapped portion is that by configuring the balloon catheter in this way, the step portion where the outside diameter changes in the overlapped portion becomes positioned inside the neck portion. Due to this, the insertability of the balloon catheter is further improved.

The recess is preferably formed by making part of the outer circumference of the distal end of the first tubular member deform along the axial direction. By forming the recess by making the distal end of the tubular member deform, the mechanical strength of the distal end of the tubular member is increased.

The axial length of the recess is preferably longer than the length of the overlapped portion. Further, in the second aspect of the present invention, the axial length of the tapered portion where the outside diameter becomes smaller toward the distal end of the first tubular member preferably is longer than the length of the overlapped portion. By configuring the balloon unit in this way, the mechanical strength between the neck portion and the tubular member at the proximal end side from the neck portion can be improved without making the outside diameter of the axial direction overlapped portion too thick. Further, it becomes easy to take out the guidewire from the proximal end opening of the guidewire lumen formed in the second tubular member.

Further, the proximal end opening of the guidewire lumen formed in the second tubular member is preferably an inclined opening obtained by cutting the end of the tubular member at a slant angle. It becomes easy to take out the guidewire from the slanted opening.

The first tubular member and the second tubular member may be made the same material, but preferably are made of different materials. For example, the second tubular member is preferably configured by a material superior in flexibility (including "pliability") compared with the first tubular member. Alternatively, the material of the first tubular member is preferably a material of a higher hardness than the second tubular member. By configuring the invention in this way, the flexibility of the balloon catheter is improved at the distal end side and therefore the insertability of the balloon catheter into a blood vessel etc. is improved. Further, the outside diameter of the second tubular member is preferably smaller than a reference outside diameter of the first tubular member. By configuring the invention in this way, the flexibility of the second tubular member is improved compared with the first tubular member. When forming the recess at the distal end of the first tubular member, the "reference outside diameter" means the outside diameter of the portion where the recess is not formed, while when forming a taper, it means the maximum outside diameter.

As the means for joining the first tubular member and the second tubular member, it is possible to use the means such as adhesion, heat bonding, etc. As the means for directly or indirectly joining the proximal end neck portion of the balloon unit to at least part of the overlapped portion from the outside, it is possible to use the means such as adhesion, heat bonding, or heat bonding using a heat shrink tube.

When a clearance arises between the tubular member and the proximal end neck portion of the balloon unit, the clearance may be filled with an adhesive, sealant, or other filler.

It is possible to wrap a reinforcing wire at least at part of the outer circumference of the overlapped portion and cover the outer circumference of this with the proximal end neck portion of the balloon unit and join the same. By using a reinforcing wire, joining different or similar tubular members which are difficult to adhere or fuse together becomes easy.

The proximal end neck portion of the balloon unit may have an inside diameter which is constant along the axial direction, but it is also possible to form it into a taper where the inside diameter becomes larger toward the proximal end side. If forming the taper, covering the neck portion over the overlapped portion becomes easy and the work efficiency is improved when producing the balloon catheter.

In the balloon catheter according to the first aspect of the present invention, the outer circumference of the distal end of the first tubular member is formed along the axial direction with a recess into which part of the outer circumference of the proximal end of the second tubular member fits. Therefore, the outside diameter of the overlapped portion between the distal end of the first tubular member and the proximal end of the second tubular member can be kept to the minimum necessary. Further, since the tubular members are joined in the proximal end neck portion of the balloon unit, a step of the joint portion is made small and the balloon catheter can be easily inserted into a blood vessel etc. Further, since the first tubular member and the second tubular member are joined at the overlapped portion, even tubular members comprised of materials difficult to adhere or heat bond together can be easily joined and there is little sharp change in hardness along the longitudinal direction.

Further, by joining the proximal end neck portion of the balloon unit so as to cover at least part of the overlapped portion, the strength of the neck portion is improved.

Further, the recess is formed at only the distal end of the first tubular member. The recess is not formed at other portions. It is therefore possible to sufficiently increase the sectional area of the flow channel of the balloon lumen formed at the first tubular member and possible to reduce the flow resistance of the lumen. Still further, at the portion where no recess is formed, it is possible to sufficiently increase the outside diameter or thickness of the first tubular member and possible to effectively prevent kinks. Further, the pushability (stiffness) of the balloon catheter is also excellent. Note that in order to further improve the mechanical strength of the first tubular member, a reinforcing wire (for example, a metal wire) may be arranged inside in the longitudinal direction or a reinforcing fiber may be braided.

In the balloon catheter according to the second aspect of the present invention, the distal end of the first tubular member has at least partially a tapered portion where the outside diameter becomes smaller toward the distal end of the first tubular member. Therefore, the outer diameter of the overlapped portion between the distal end of the first tubular member and the proximal end of the second tubular member can be kept to the minimum necessary. Further, since the tubular members are joined together in the proximal end neck portion of the balloon unit, a step of the joint portion is made small and the insertability of the balloon catheter into a blood vessel etc. is improved.

Further, since the first tubular member and the second tubular member are joined at the overlapped portion, even tubular members comprised of materials difficult to adhere or heat bond together can be easily joined and there is little sharp change in hardness along the longitudinal direction.

Further, by joining the proximal end neck portion of the balloon unit so as to cover at least part of the overlapped portion, the strength of the neck portion is improved.

Further, since there is a tapered portion where the outside diameter becomes smaller toward the distal end of the first tubular member, the portion where the sectional area of the flow channel of the balloon lumen formed at the first tubular member becomes smaller can be kept to the minimum necessary and the flow resistance of the lumen can be reduced. Still further, at the proximal end side closer than the tapered portion formed at the distal end of the first tubular member, it is possible to sufficiently increase the outside diameter or thickness of the first tubular member and possible to effectively prevent the first tubular member from kinking. Further, the pushability of the balloon catheter is also excellent. Note that in order to further improve the mechanical strength of the first tubular member, a reinforcing wire (for example, a metal wire) may be arranged inside in the longitudinal direction or a reinforcing fiber may be braided.

BRIEF DESCRIPTION OF THE DRAWINGS

FIG. 5A is a disassembled perspective view of key parts of a joined portion of a first tubular member and a second tubular member, while

FIG. 10 is sectional view of key parts of a balloon catheter 2b according to another embodiment of the present invention;

BEST MODE FOR CARRYING OUT THE INVENTION

The present invention will be explained below based on the embodiments shown in the figures.

First Embodiment

Figure 1:
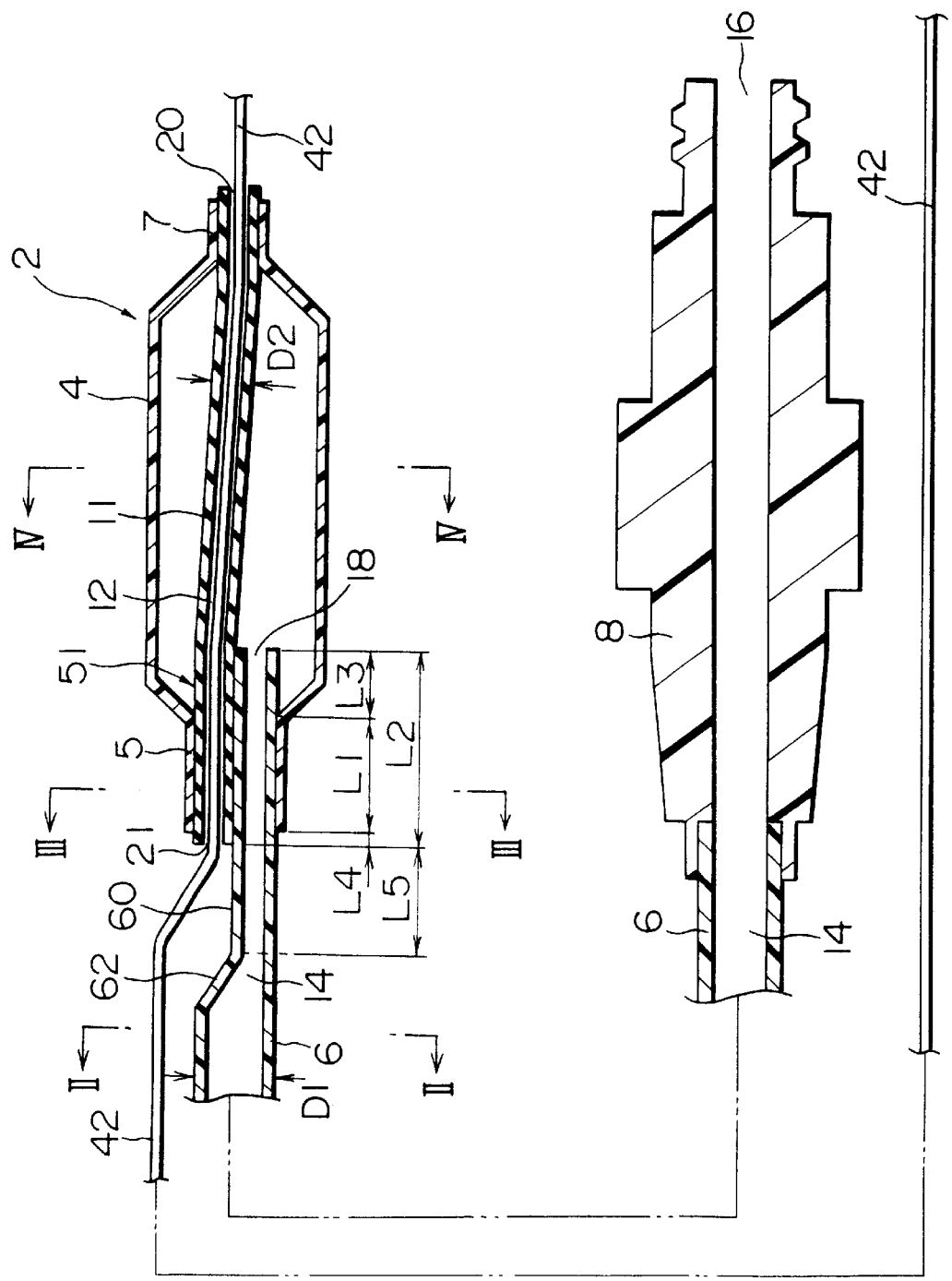
FIG. 1 is a schematic sectional view of key parts of a balloon catheter according to a first embodiment of the present invention.

The balloon catheter 2 according to the present embodiment shown in FIG. 1 is used for example for percutaneous transluminal coronary angioplasty (PTCA), dilatation of the blood vessels of the limbs etc., dilatation of the upper urinary tract, renovascular dilatation, and other methods and is used for dilatation of stenosis portions formed in the blood vessels or other body cavities. In the following explanation, the explanation is given taking as an example the case of use of the balloon catheter of the present embodiment for PTCA.

The dilatation use balloon catheter 2 of the present embodiment is a so-called monorail type balloon catheter and is comprised of a balloon unit 4, first tubular member 6 used as a catheter tube, and connector 8.

Figure 5A:
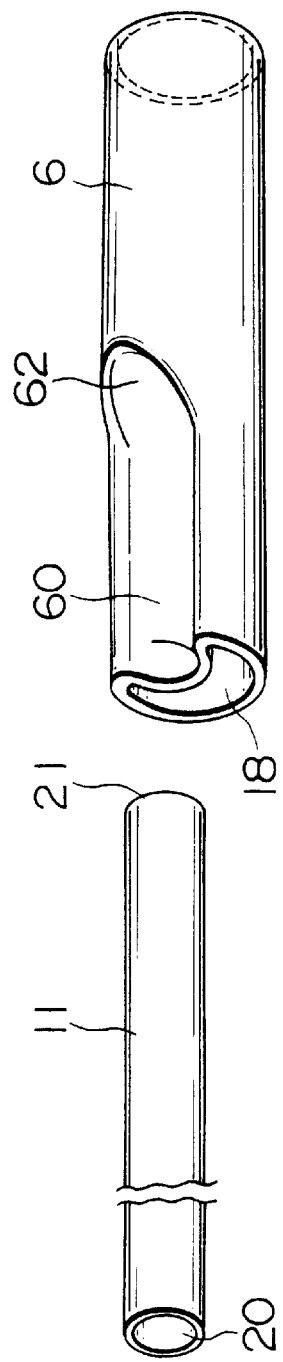

In the present embodiment, the distal end of the first tubular member 6 is formed with a recess 60 along the axial direction by deforming part of the outer circumference of the distal end of the circular tube comprising the tubular member along the axial direction as shown in FIG. 5A. The recess 60 is a portion of an outside diameter smaller than the outside diameter of the first tubular member. Further, an inclined face 62 is formed at the terminal part of the recess 60 in the axial direction. The proximal end of the second tubular member 11 can be fit in the recess 60. The inside diameter of the recess 60 is preferably about the outside diameter of the second tubular member 11. The depth of the recess 60, when the proximal end of the second tubular member 11 is fit in the recess 60, as shown in FIG. 3, is preferably a depth of an extent covering at least about ⅓ of the outer circumference of the second tubular member 11, preferably at least ½.

Figure 5B:
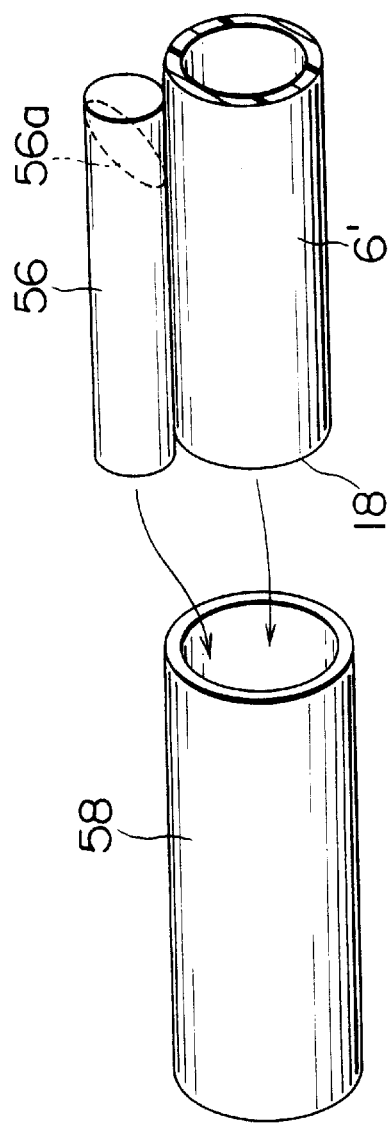
FIG. 5B is a perspective view of key parts of an example of the method for forming a recess in a distal end of the first tubular member.

To form the recess 60 shown in FIG. 5A at the distal end of the first tubular member 6, for example, first, as shown in FIG. 5B, a tube 6' of a circular cross-section serving as the first tubular member 6 is formed. Next, the distal end of the tube 6' and a metal rod 56 of an outside diameter substantially the same as the outside diameter of the second tubular member 11 are inserted into a tube-shaped metal mold 58 and shaped by heating. Next, after the end of the tube 6' is taken out from the metal mold 58 and the metal rod 56 is removed, the recess 60 shown in FIG. 5A is formed. Note that as shown in FIG. 5B, by forming the inclined face 56a at the rear end of the metal rod 56, it is possible to control the angle of inclination of the inclined face 62 shown in FIG. 5A. The inside diameter of the metal mold 58 is substantially the same as or slightly larger than the outside diameter of the tube 6'.

Figure 3:
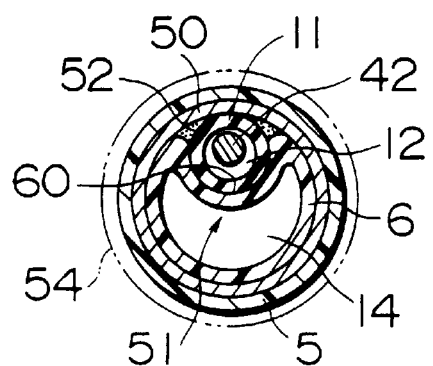
FIG. 3 is a sectional view of key parts along the line III—III of FIG. 1.

As shown in FIGS. 1 and 3, the proximal end of the second tubular member 11 is accommodated in the recess 60 formed at the distal end of the first tubular member 6, and an overlapped portion 51 of the first tubular member 6 and second tubular member 11 is formed along the axial direction. The axial length of the overlapped portion 51 is made L2.

The outer circumference of the overlapped portion 51, as shown in FIG. 3, has a reinforcing wire 50 wound around it in accordance with need. The distal end of the first tubular member 6 and the proximal end of the second tubular member 11 are joined at the overlapped portion 51. An adhesive or sealant or other filler is filled in the clearance between the first tubular member 6 and the second tubular member 11 and the clearance with the reinforcing wire 50 to join these members while sealing them. The reinforcing wire 50 may be wound around the entire portion of the outer circumference of the overlapped portion 51 along the axial direction or at only part. Further, when comprising the first tubular member 6 and the second tubular member 11 by a combination of materials able to be easily joined by adhesion or heat bonding, the reinforcing wire 50 need not necessarily be provided.

The proximal end neck portion 5 of the balloon unit 4 is joined to part of the outer circumference of the overlapped portion 51 in the axial direction through the reinforcing wire 50 or not through the reinforcing wire 50. The neck portion 5 may be joined by an adhesive, by heat bonding, or by a heat shrink tube 54. Further, the proximal end neck portion 5 of the balloon unit 4 may be joined simultaneously with the joining of the first tubular member 6 and second tubular member 11. The heat shrink tube 54 may be removed after joining. Note that the axial length of the neck portion 5 is designated as L1 (see FIG. 1).

As shown in FIG. 1, the distal end neck portion 7 of the balloon unit 4 is joined to the outer circumference of the distal end of the second tubular member 11 by any of the means of heat bonding, adhesion, or joining by a heat shrink tube. The inner space of the balloon unit 4 forms a sealed space except for being communicated with the distal end opening 18 of the first tubular member 6. Further, the proximal end of the first tubular member 6 has a connector 8 connected to it.

Figure 4:
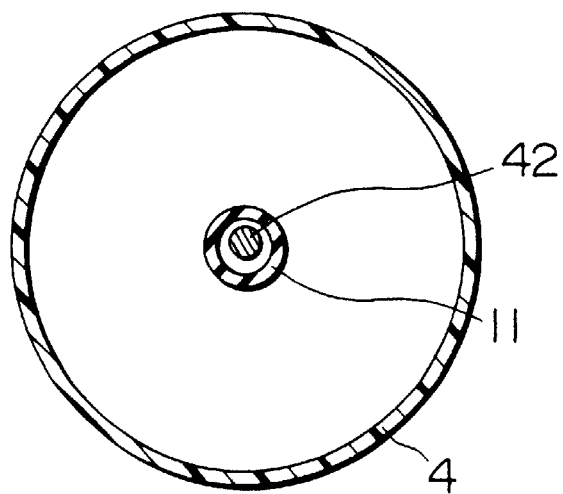
FIG. 4 is a sectional view of key parts along the line IV—IV of FIG. 1.

The balloon unit 4 is comprised of a tubular film member reduced in diameter at the two ends. The film thickness is not particularly limited, but may be 15 to 300 μm, preferably 30 to 150 μm. The balloon unit 4 is not particularly limited, so long as it is tubular. A cylindrical or polylateral tubular shape are also possible. Further, the outside diameter of the balloon unit 4 at the time of inflation is determined by factors such as the inside diameter of the blood vessel and normally is 1.5 to 10.00 mm or so, preferably 3 to 7 mm. The axial length of the balloon unit 4 is determined by factors such as the size of the stenosis portion in the blood vessel and is not particularly limited, but may be 15 to 50 mm, preferably 20 to 40 mm. The balloon unit 4 before inflation is folded and wrapped around the overlapped portion 51 and the second tubular member 11 so that the outside diameter is reduced as much as possible. Note that the state where the balloon unit 4 is inflated is shown in FIG. 4. As shown in FIG. 4, the axial center of the balloon unit 4 and the axial center of the second tubular member 11 are preferably concentric, but they do not necessarily have to be concentric.

The material comprising the balloon unit 4 is preferably a material having a certain degree of flexibility. For example, polyethylene, polyethylene terephthalate, polypropylene, ethylene-propylene copolymer, or other copolymer between ethylene and another α-olefin, ethylene-vinyl acetate copolymer, polyvinyl chloride (PVC), cross-linkable ethylene-vinyl acetate copolymer, polyurethane, polyamide, polyamide elastomer, polyimide, polyimide elastomer, silicone rubber, natural rubber, etc. may be used. Preferably, it is made of polyethylene, polyethylene terephthalate, or polyamide.

The first tubular member 6 may be comprised of a material similar to the balloon unit 4 for example, but preferably is comprised of a material having flexibility. For example, polyethylene, polyethylene terephthalate, polypropylene, ethylene-propylene copolymer, ethylene-vinyl acetate copolymer, polyvinyl chloride (PVC), cross-linkable ethylene-vinyl acetate copolymer, polyurethane, polyamide, polyamide elastomer, polyimide, polyimide elastomer, silicone rubber, natural rubber, etc. may be used. Preferably, it is made of polyethylene, polyamide, or polyimide. Further, the second tubular member 11 may be comprised of a material the same as the first tubular member 6, but is preferably formed by another material. For example, the second tubular member 11 is preferably comprised of a plastic softer than the first tubular member 6.

As the soft plastic comprising the second tubular member 11, polyurethane, polyamide, polyimide, polyethylene, or other plastic having a JIS hardness of 70A to 95A can be used. As the hard plastic comprising the first tubular member 6, polyurethane, polyamide, polyimide, polyethylene, or other plastic having a JIS hardness of 50D to 75D may be used.

Inside of the second tubular member 11 is formed a guidewire lumen 12 along the longitudinal direction. The distal end opening 20 and the proximal end opening 21 are communicated with the outside. The guidewire lumen 12 is a portion into which the guidewire 42 is inserted through the distal end opening 20 and the proximal end opening 21. The inside diameter is not particularly limited so long as it is a diameter which enables the guidewire 42 to be inserted and is for example 0.15 to 1.0 mm, preferably 0.25 to 0.6 mm. The inside diameter of the lumen 14 is preferably uniform along the axial direction. Further, the thickness of the second tubular member 11 is determined so as to give the mechanical strength necessary for the second tubular member 11 and is preferably 20 to 400 μm, more preferably 40 to 150 μm.

Further, the inside of the first tubular member 6 is formed with a balloon lumen 14 along the longitudinal direction. The balloon lumen 14 is communicated with an inflation port 16 formed at the connector 8. A pressurized fluid is introduced from there. The pressurized fluid is introduced into the balloon through the distal end opening 18 of the first tubular member 6 so as to make the folded balloon unit 4 inflate.

The pressurized fluid introduced into the balloon lumen 14 through the inflation port 16 is not particularly limited, but for example use may be made of a 50/50 (weight ratio) mixed aqueous solution of a radiopaque medium and a saline solution. A radioopaque medium is included for obtaining images of positions of the balloon unit 4 and the first tubular member 6 using radioactivity when using the balloon catheter 2. The pressure of the pressurized fluid for inflating the balloon unit 4 is not particularly limited, but in terms of absolute pressure is 3 to 12 atm, preferably 4 to 8 atm or so.

The connector 8 shown in FIG. 1 is for example suitably formed by polycarbonate, polyamide, polysulfone, polyacrylate, methacrylate-butylene-styrene copolymer, or another thermoplastic resin.

The balloon lumen 14 has a flow channel of a circular cross-section at the portion other than the recess 60 formed at the outer circumference of the distal end of the first tubular member 6. The inside diameter is preferably 0.3 to 3 mm, more preferably 0.5 to 1.5 mm. Further, the thickness of the first tubular member 6 is determined so as to give the mechanical strength necessary as the first tubular member 6 and is preferably 40 to 500 mm, more preferably 80 to 300 mm.

Figure 2:
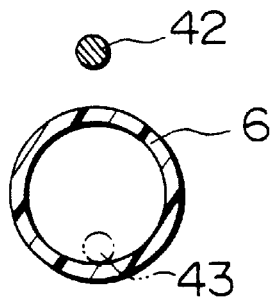
FIG. 2 is a sectional view of key parts along the line II—II of FIG. 1.

The first tubular member 6 is a portion inserted along the inside of a twisting blood vessel and is required to have flexibility. Further, the first tubular member 6 is also a portion for transmitting the operating force for positioning the balloon unit 4 at a predetermined position in the blood vessel. Therefore, the first tubular member 6 is required to have a suitable flexibility and a strength (pushability) of an extent enabling transmission of the operating force without kinking. As the tube unit comprising the first tubular member 6, when the pushability is insufficient, as shown in FIG. 2, a reinforcing metal wire 43 may be inserted into the lumen 14 of the first tubular member 6.

In the present embodiment, the outside diameter D1 of the first tubular member 6 at the portion where the recess 60 is not formed is preferably larger than the outside diameter D2 of the second tubular member 11, preferably larger by about 30 to 100 percent of D2. By configuring the invention in this way, the flexibility is improved at the distal end side of the balloon catheter 2 and the insertion of the balloon catheter 2 into a blood vessel becomes easier. Further, the sectional area of the flow channel of the balloon lumen 14 of the first tubular member 6 can be made larger.

In the present embodiment, the axial length L2 of the overlapped portion 51 shown in FIG. 1 is preferably 2 to 500 mm. If the length of the overlapped portion is too short, the strength of the joined portion of the tubular members tends to become insufficient, while if too long, the material is wasted. Further, the axial length L1 of the proximal end neck portion 5 of the balloon unit 4 is configured to be shorter than the axial length of the overlapped portion and is a length of about 100 to 300 mm.

Further, the length L3 by which the distal end of the first tubular member 6 projects from the neck portion 5 inside the balloon unit 4, while depending on the length of the balloon unit, is 0 to 10 mm in the present embodiment. If the length L3 is too long, the portion where the second tubular member 11 exists alone becomes too short, which is undesirable. Further, the length L4 by which the proximal end of the second tubular member 11 projects out from the proximal end of the neck portion 5 is 0 to 500 mm, preferably 50 to 350 mm. If the length L4 is too large, the effect of shortening the length of the guidewire 42 extending outside the body by using a monorail type balloon catheter becomes smaller.

Figure 6:
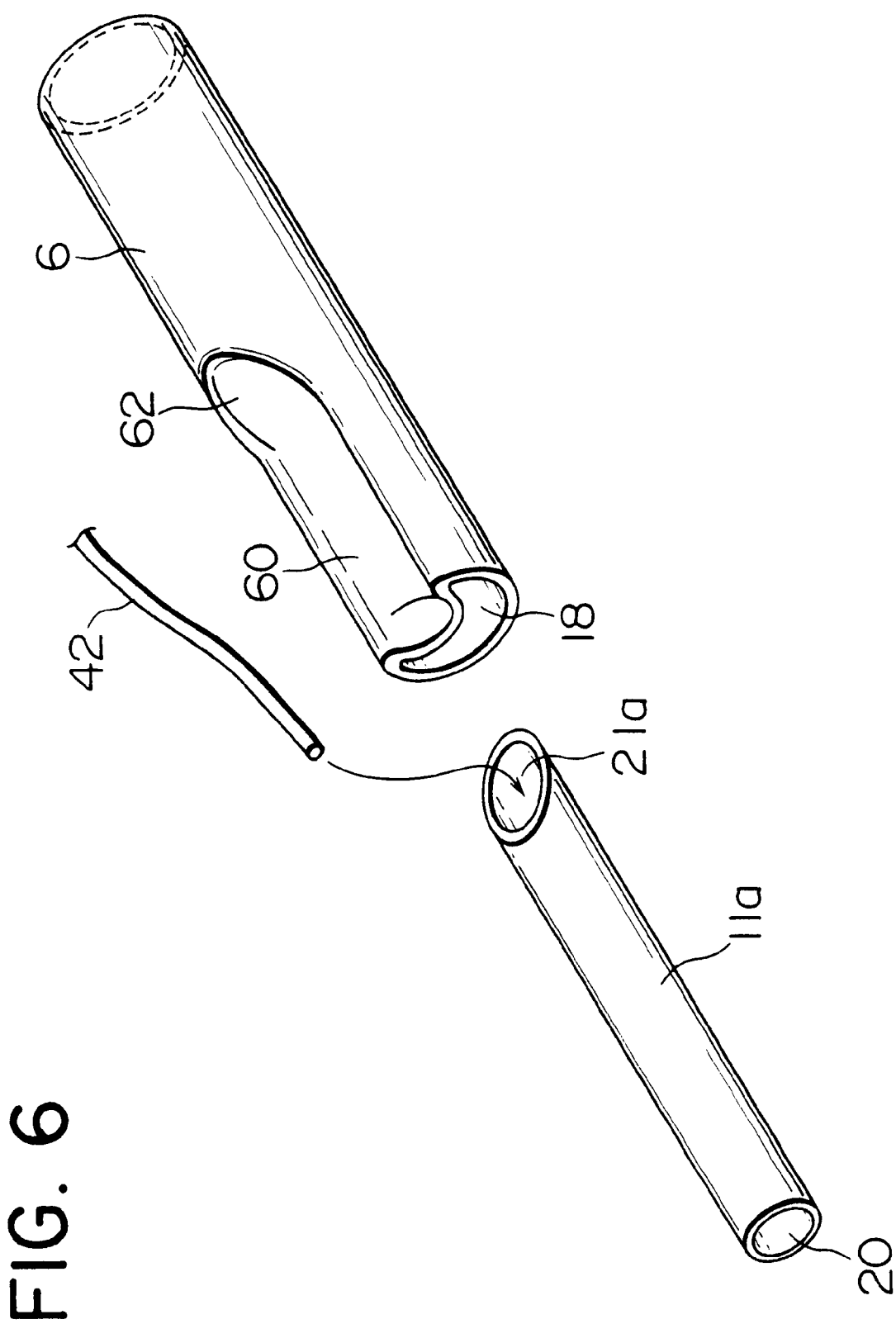
FIG. 6 is a disassembled perspective view of key parts of a joined portion of a first tubular member and second tubular member according to another embodiment of the present invention.

Further, the axial length of the recess 60 formed at the distal end of the first tubular member 6 is preferably longer by exactly the predetermined distance L5 than the axial length L2 of the overlapped portion 51. The predetermined distance L5 in this case is preferably 2 to 300 mm. By giving this predetermined distance L5, the extraction of the guidewire 42 from the proximal end opening 21 of the second tubular member 11 or the insertion thereof becomes smooth. Further, as shown in FIG. 6, by means of making the end face of the proximal end opening 21a of the second tubular member 11a an inclined face, the extraction of the guidewire 42 from the proximal end opening 21a or its insertion becomes smooth.

Next, an explanation will be given of the method of PTCA treatment using the balloon catheter 2 of the embodiment shown in FIG. 1.

First, the air in the balloon catheter 2 is removed as much as possible. Next, a syringe or other suction and injecting means is attached to the inflation port 16 of the connector 8, a blood imaging agent (for example, containing iodine) or other fluid is injected into the syringe, and suction and injection are repeated to replace the air in the balloon lumen 14 and the balloon unit 4 with the fluid.

Figure 7:
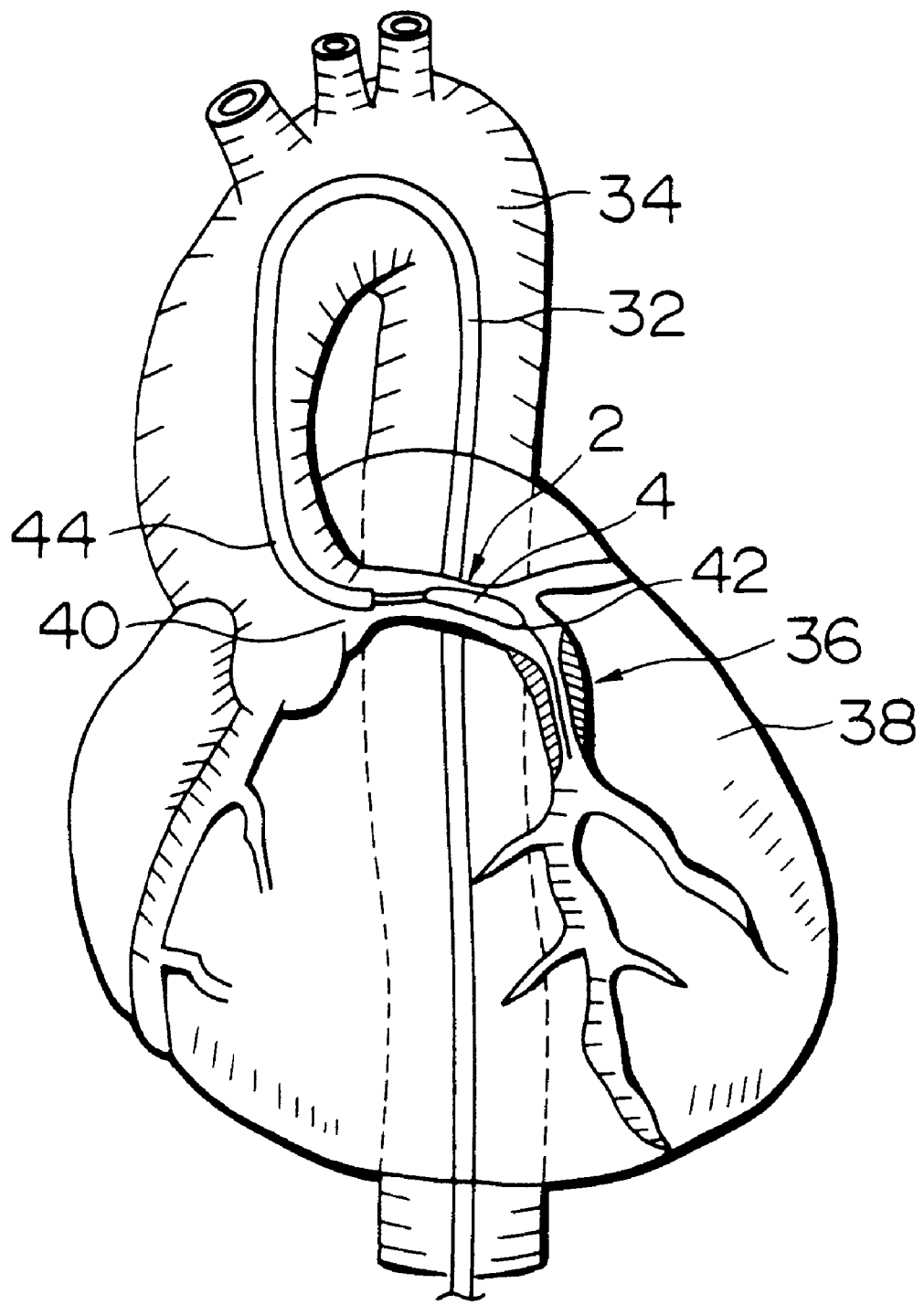
FIG. 7 is a schematic view of a position of use of a balloon catheter.

To insert the balloon catheter 2 in an arterial blood vessel, first, the Selzinger method etc. is used to insert a guide catheter guidewire (not shown) into the blood vessel so that its tip reaches close to for example the heart. Next, the guide catheter 32 shown in FIG. 7 is inserted into the arterial blood vessel 34 along the guide catheter guidewire to position the tip at the coronary artery inlet 40 of the heart 38 having a stenosis portion 36. Note that the stenosis portion 36 is formed by for example a thrombus or arteriosclerosis etc.

Next, only the guide catheter guidewire is removed, a balloon catheter guidewire 42 thinner than that is inserted along the guide catheter 32, and the tip is inserted up to a position passing through the stenosis portion 36.

Next, the distal end of the guidewire 42 is inserted into the distal end opening 20 of the balloon catheter 2 shown in FIG. 1, passed through the inside of the guidewire lumen 12, and pulled out from the proximal end opening 21. In the state with the balloon unit 4 folded, the balloon catheter 2 is passed through the inside of the guide catheter 32 shown in FIG. 7 along the guidewire 42. The balloon unit 4 of the balloon catheter 2 is inserted to just before the stenosis portion 36 as shown in FIG. 7.

Figure 8A:
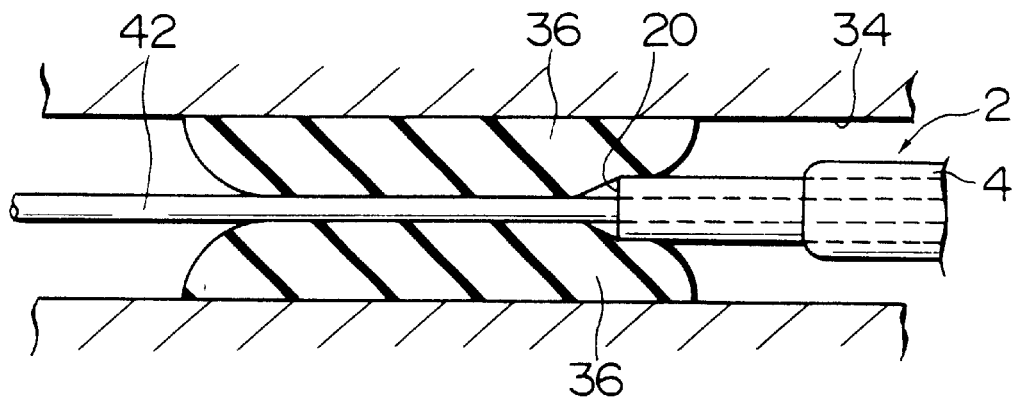
FIGS. 8A to 8C are sectional views of key parts of the state of use of a balloon catheter.
Figure 8B:
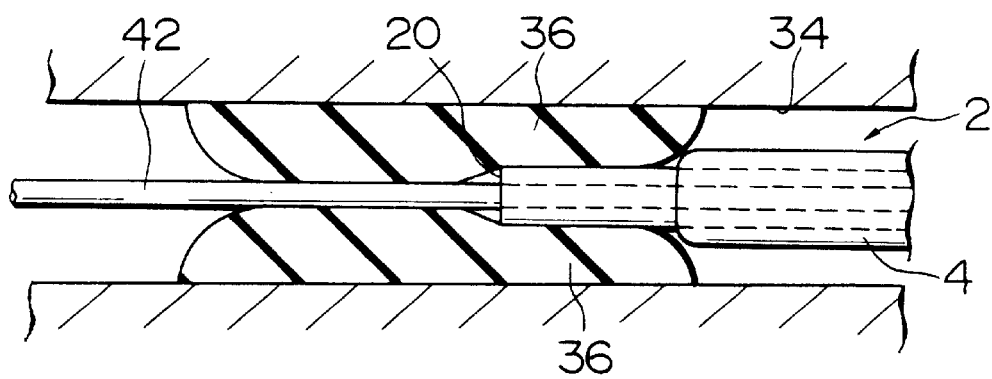

Next, as shown in FIGS. 8A and 8B, the folded balloon unit 4 of the balloon catheter 2 is inserted into the stenosis portion 36 along the guidewire 42.

Figure 8C:
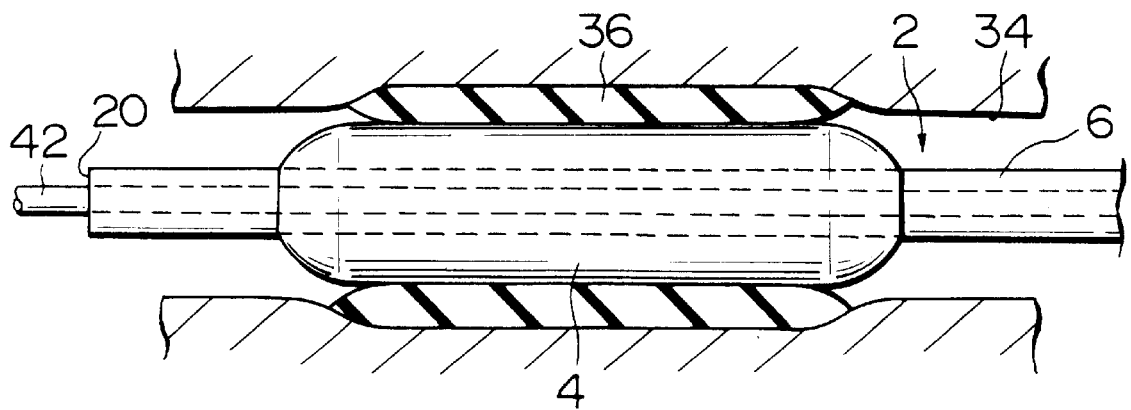

Next, as shown in FIG. 8C, the balloon unit 4 is accurately positioned at the center of the stenosis portion 36 while observing the position of the balloon unit 4 by an x-ray fluoroscope etc. By inflating the balloon unit 4 at that position, the stenosis portion 36 of the blood vessel 32 is dilated and good treatment becomes possible. Note that to inflate the balloon unit 4, fluid is injected into the balloon unit 4 from the inflation port 16 shown in FIG. 1 through the balloon lumen 14.

The time for inflating the balloon unit is not particularly limited, but for example is about 1 minute. Next, the fluid is drained out from the balloon unit quickly to make the balloon unit shrink and secure the flow of blood at the terminal side of the dilated stenosis portion 36. The stenosis portion 36 must be dilated in stages so as not to damage the blood vessel 34. First, a balloon catheter 2 with a small outside diameter balloon unit 4 is inserted along the guidewire 42 and then is exchanged with balloon catheters 2 having successively larger outside diameter balloon units 4. At that time, since the balloon catheter 2 according to the present embodiment is a monorail type balloon catheter, the balloon catheters can be exchanged by just extending the proximal end of the guidewire 42 outside the body to an extent slightly longer than a portion corresponding to the length of the guidewire lumen 12.

In the balloon catheter 2 according to the present embodiment, the outer circumference of the distal end of the first tubular member is formed along the axial direction with a recess 60 into which part of the outer circumference of the proximal end of the second tubular member 11 fits. Therefore, the outside diameter of the overlapped portion 51 of the distal end of the first tubular member 6 and the proximal end of the second tubular member 11 can be kept to the minimum necessary. Further, since the tubular members 6 and 11 are joined in the proximal end neck portion 5 of the balloon unit 4, a step of the joint portion is small and the insertability of the balloon catheter 2 into the blood vessel etc. is improved.

Further, by joining the proximal end neck portion 5 of the balloon unit so as to cover at least part of the overlapped portion 51, the strength of the neck portion 5 is improved.

Further, the recess 60 is formed at only the distal end of the first tubular member 6. The recess 60 is not formed at other portions. It is therefore possible to sufficiently increase the sectional area of the flow channel of the balloon lumen 14 formed at the first tubular member 6 and possible to reduce the flow resistance of the lumen 14. Still further, at the portion where no recess 60 is formed, it is possible to sufficiently increase the outside diameter or thickness of the first tubular member 6 and possible to effectively prevent kinks in the first tubular member 6. Further, the pushability of the balloon catheter 2 is also excellent.

Second Embodiment

Figure 9:
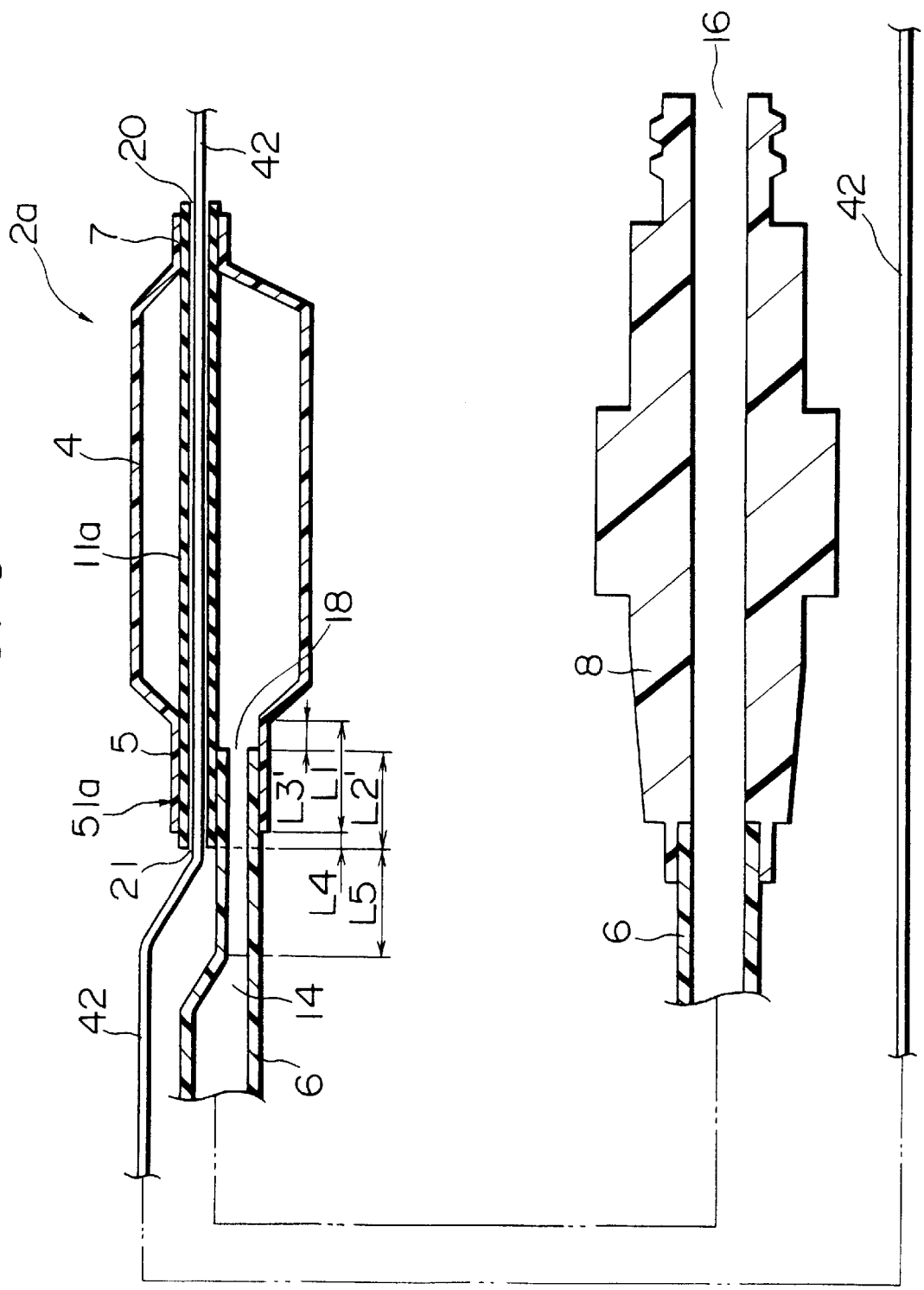
FIG. 9 is a schematic sectional view of key parts of a balloon catheter according to another embodiment of the present invention.

FIG. 9 is a schematic sectional view of key parts of the balloon catheter according to another embodiment of the present invention. As shown in FIG. 9, the balloon catheter 2a according to the present embodiment is a modification of the balloon catheter 2 shown in FIG. 1. The second tubular member 11a is arranged straight in the axial direction, while the axial length L2' of the overlapped portion 51a between the first tubular member 6 and the second tubular member 11a is made shorter than the length L1 of the proximal end neck portion 5. Other than this, it has the same configuration as the balloon catheter 2 shown in FIG. 1, so the common members are assigned common part numbers and explanations thereof are partially omitted.

In the present embodiment, the axial length L2' of the overlapped portion 51a is about 200 to 250 mm. The distal end opening 18 of the first tubular member 6 is positioned at the position of the distance L3' from the inside end of the balloon of the neck portion 5. This distance L3' is preferably about 20 to 80 percent of the axial length L1 of the neck portion 5. By positioning the distal end opening 18 of the first tubular member 6 inside the neck portion 5 in the axial direction in this way, the step portion where the outside diameter changes at the overlapped portion 51a is positioned inside the neck portion 5 and the insertability of the balloon catheter 2a is further improved.

The rest of the configuration, action, and effect of the balloon catheter 2a according to the present embodiment are similar to the case of the first embodiment.

Third Embodiment

FIG. 10 is a sectional view of key parts of the balloon catheter 2b according to another embodiment of the present invention. As shown in FIG. 10, the balloon catheter 2b according to the present embodiment is a modification of the balloon catheter 2 or 2a shown in FIG. 1 or FIG. 9. The distal end of the first tubular member 6b is formed with a tapered portion where the outside diameter becomes smaller toward the distal end, while the second tubular member 11b is configured as a tapered tube where the outside diameter and the inside diameter become smaller toward the proximal end. Other than this, it has the same configuration as the balloon catheter 2 shown in FIG. 1 or the balloon catheter 2a shown in FIG. 9, so the common members are assigned common part numbers and explanations thereof are partially omitted.

In the present embodiment, the balloon lumen 14b formed along the axial direction inside the first tubular member 6b becomes smaller in a taper toward the distal end side. Further, the guidewire lumen 12b formed along the axial direction inside the second tubular member 11b becomes smaller toward the proximal end side.

The taper angles of these tubular members 6b and 11b are not particularly limited, but are taper angles of an extent where the outside diameter or the inside diameter becomes 0 to 50 percent smaller per 100 mm unit length along the axial direction. The minimum inside diameter portion at the guidewire lumen 12b is formed at the position of the proximal end opening 21 of the second tubular member 11b. The minimum inside diameter is determined to an extent enabling the guidewire 42 to be inserted. Further, the minimum inside diameter at the balloon lumen 6b is formed at the position of the distal end opening 18 of the first tubular member 6b. The minimum inside diameter is determined so that the pressurized fluid can be introduced inside the balloon unit 4 with no problem. Note that the tapered portion of the tubular member 6b can be formed by pulling the end of the tube in the axial direction while heating it. Further, the tapered tube comprising the tubular member 11b may be formed by changing the pull out speed with a constant extrusion speed at the time of formation by extrusion etc.

Figure 11A:
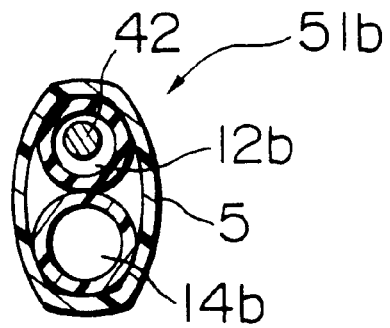
FIGS. 11A to 11C are cross sectional views of an overlapped portion of a balloon catheter according to another embodiment of the present invention.

In the balloon catheter 2b according to the present embodiment, the distal end of the first tubular member 6b has a tapered portion where the outside diameter becomes smaller toward the distal end of the first tubular member 6b and the second tubular member 11b is comprised of a tapered tube where the outside diameter and the inside diameter become smaller toward the proximal end. Therefore, the increase in the outside diameter of the overlapped portion 51b of the distal end of the first tubular member 6b and the proximal end of the second tubular member 11b can be kept to the minimum necessary. The sectional area of the overlapped portion 51b is shown in FIG. 11A.

Further, in the present embodiment, since the tubular members 6b and 11b are joined at the proximal end neck portion 5 of the balloon unit 4, the step portion is small, and the balloon catheter 2b can be easily inserted into the blood vessel etc.

Further, since the first tubular member 6b and the second tubular member 11b are joined at the overlapped portion 51b, even tubular members 6b and 11b comprised of materials difficult to adhere or heat bond can be easily joined and there is little sharp change in hardness along the longitudinal direction.

Further, by joining the proximal end neck portion 5 of the balloon unit 4 so as to cover at least part of the overlapped portion 51b, the strength of the neck portion 5 is improved.

Further, since there is a tapered portion where the outside diameter becomes smaller toward the distal end of the first tubular member 6b, the portion where the sectional area of the flow channel of the balloon lumen 6b formed at the first tubular member 6b becomes smaller can be kept to the minimum necessary and the flow resistance of the lumen 6b can be reduced. Still further, at the proximal end side from the tapered portion formed at the distal end of the first tubular member 6b, it is possible to sufficiently increase the outside diameter or thickness of the first tubular member 6b and possible to effectively prevent kinks. Further, the pushability of the balloon catheter 2b is also excellent.

The rest of the configuration, action, and effect of the balloon catheter 2b according to the present embodiment are similar to the case of the first embodiment.

Other Embodiments

Note that the present invention is not limited to the above embodiments and may be changed in various ways within the scope of the present invention.

Figure 11B:
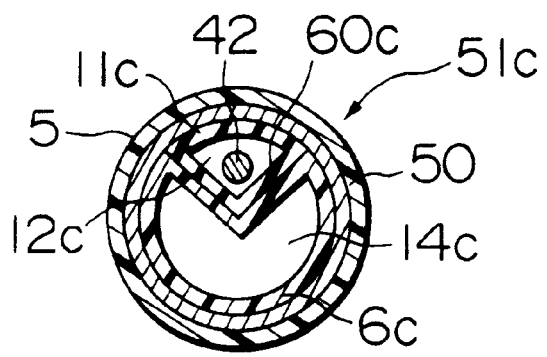

For example, as shown in FIG. 11B, the sectional shape of the recess 60c formed at the overlapped portion 51c of the distal end of the first tubular member 6c may be made a fan-shape(sector-shape) and the sectional shape of the distal end of the second tubular member 11c may be formed into the same fan-shape. In this case, the clearance between these tubular members 6c and 11c becomes smaller. Note that the shapes of the lumens 12c and 14c also become fan shaped.

Figure 11C:
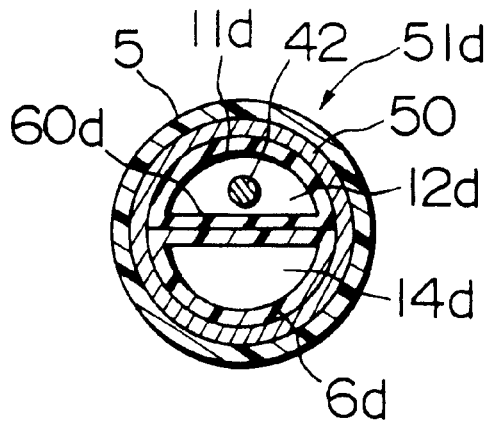

Further, as shown in FIG. 11C, the sectional shape of the recess 60d formed at the overlapped portion 51d of the distal end of the first tubular member 6d may be made a semicircular shape and the sectional shape of the distal end of the second tubular member 11d may be formed into the same semicircular shape. In this case as well, the clearance between these tubular members 6d and 11d becomes smaller. Note that the shapes of the lumens 12d and 14d also become semicircular.

Figure 12:
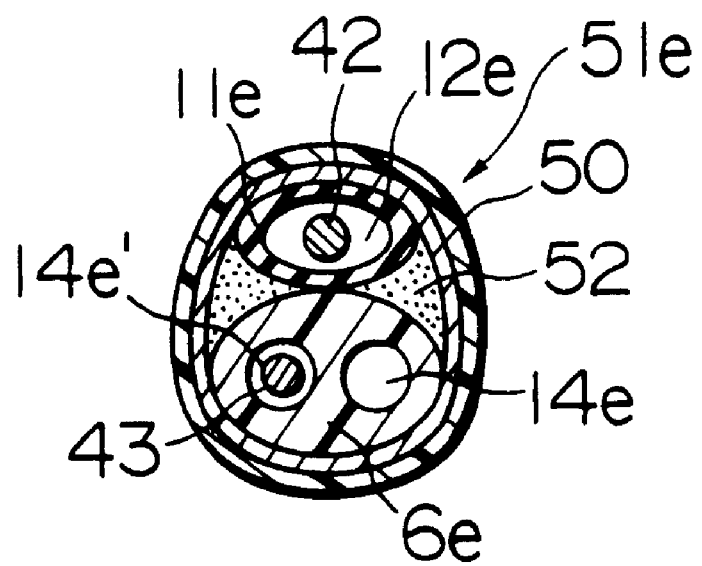
FIG. 12 is a cross sectional view of an overlapped portion of a balloon catheter according to another embodiment of the present invention.

Further, as shown in FIG. 12, the first tubular member 6e is comprised of a multi-lumen tube having two or more lumens 14e and 14e' along the entire length. One lumen 14e among these is made the balloon lumen. A reinforcing metal wire 43 may be inserted into the other lumen 14e' along the longitudinal direction of the first tubular member 6e. Note that in the present embodiment, as the first tubular member 6e, use was made of the multi-lumen tube with elliptical sectional shape at least at the overlapped portion 51e, but the sectional shape of the first tubular member 6e is not limited to an elliptical shape and may be circular or another shape as well.

Further, in the present embodiment, at least at the overlapped portion 51e, the sectional shape of the second tubular member 11e having the guidewire lumen 12e is also made elliptical, but is not limited to an elliptical shape and may be circular or another shape as well. A reinforcing wire 50 is in accordance with need wound around the outer circumference of the overlapped portion 51e of the first tubular member 6e and second tubular member 11e. An adhesive or sealant or other filler 52 is filled in the clearance between the first tubular member 6e and the second tubular member 11e and the clearance with the reinforcing wire 50 to join these while sealing them.

In the balloon catheter according to the present embodiment, not only are actions similar to the balloon catheter according to the previous embodiment exhibited, but also the strength or ease of flexing of the first tubular member 6e can be adjusted by the reinforcing metal wire 43 inserted in the lumen 14e'.

Figure 13:
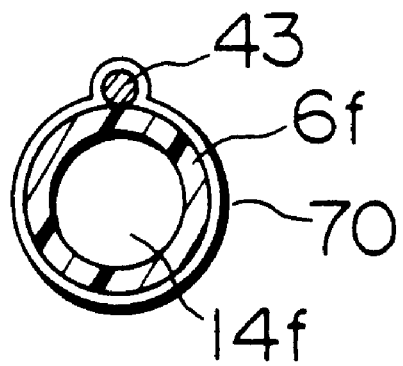
FIG. 13 is a cross sectional view of a first tubular member of a balloon catheter according to another embodiment of the present invention.

FIG. 13 is a sectional view of a first tubular member 6f of the balloon catheter according to another embodiment of the present invention. In this embodiment, a reinforcing metal wire 43 is arranged at the outer circumference of the first tubular member 6f formed with the balloon lumen 14F along the longitudinal direction straight or in a spiral. The outer circumference of the first tubular member 6f including the reinforcing metal wire 43 integrally is covered with the heat shrink tube 70.

The heat shrink tube 70 is not particularly limited. Silicone, ethylene-vinyl acetate copolymer, polyvinyl chloride, ethylene tetrafluoride-propylene hexafluoride copolymer (FEP), ethylene tetrafluoride-ethylene copolymer resin (EFTE), and other fluororesins etc. may be used. Among these, silicone is preferable.

In the balloon catheter according to the present embodiment, not only are actions similar to the balloon catheter according to the previous embodiment exhibited, but also the strength or ease of flexing of the first tubular member 6f can be adjusted by the reinforcing metal wire 43 formed integrally with the outer circumference of the first tubular member 6f covered with the heat shrink tube 70.

Note that the balloon catheter according to the present invention is not limited in specific application to PTCA treatment. It may be used for other treatment as well.

CAPABILITY OF EXPLOITATION IN INDUSTRY

The balloon catheter of the present invention is suitable as a balloon catheter for dilatation of a blood vessel. In particular, it is suitable as a balloon catheter for PTCA.

What is claimed is:

1. A balloon catheter comprising:
    a first tubular member in which at least one balloon lumen is formed inside along a longitudinal direction thereof;
    a balloon unit which is communicated internally with the balloon lumen formed in the first tubular member and capable of being expanded by a fluid fed through that balloon lumen; and
    a second tubular member extending axially inside the balloon unit and provided axially therein with at least one guidewire lumen;
    a distal end of the balloon unit connected with a distal end of the second tubular member;
    an overlapped portion formed by overlapping and substantially contacting outer circumference of a proximal end of said second tubular member with outer circumference of a distal end of said first tubular member axially over a predetermined distance;
    a neck portion of a proximal end side of said balloon unit connected with at least part of said overlapped portion so as to cover at least part of said overlapped portion; and
    a portion of an outside diameter on the distal end of the first tubular member being smaller than an outside diameter of the proximal end of the first tubular member.

2. A balloon catheter comprising:
    a first tubular member in which at least one balloon lumen is formed inside along a longitudinal direction thereof;
    a balloon unit which is communicated internally with the balloon lumen formed in the first tubular member and capable of being expanded by a fluid fed through that balloon lumen;
    a second tubular member extending axially inside the balloon unit and provided axially therein with at least one guidewire lumen;
    a distal end of the balloon unit connected with a distal end of said second tubular member;
    an overlapped portion formed by overlapping and substantially contacting outer circumference of a proximal end of said second tubular member with outer circumference of a distal end of said first tubular member axially over a predetermined distance;
    a neck portion of a proximal end side of said balloon unit connected with at least part of said overlapped portion so as to cover at least part of said overlapped portion; and
    a recess in which a part of an outer circumference of the proximal end of the second tubular member is received and which is formed axially on an outer circumference of the distal end of said first tubular member.

3. The balloon catheter as set forth in claim 2, wherein said recess is formed by deforming axially a part of the outer circumference of the proximal end of the first tubular member and the axial length of the recess is longer than the length of the overlapped portion.

4. The balloon catheter as set forth in claim 2, wherein an inside diameter of the recess is substantially the same as an outside diameter of the second tubular member and a depth of the recess is a depth of an extent surrounding at least ⅓ of the outer circumference of the second tubular member when the proximal end of the second tubular member is fit in the recess.

5. A balloon catheter comprising:
    a first tubular member in which at least one balloon lumen is formed inside along a longitudinal direction thereof;
    a balloon unit which is communicated internally with the balloon lumen formed in the first tubular member and capable of being expanded by a fluid fed through that balloon lumen; and
    a second tubular member extending axially inside the balloon unit and provided axially therein with at least one guidewire lumen;
    a distal end of the balloon unit connected with a distal end of said second tubular member;
    an overlapped portion formed by overlapping and substantially contacting outer circumference of a proximal end of said second tubular member with outer circumference of a distal end of said first tubular member axially over a predetermined distance;
    a neck portion of a proximal end side of said balloon unit connected with at least part of said overlapped portion so as to cover at least part of said overlapped portion; and
    a tapered portion where the outside diameter becomes smaller toward the distal end of the first tubular member.

6. The balloon catheter as set forth in claim 5, wherein said second tubular member has at least partially a tapered portion where the outside diameter becomes smaller toward the proximal end of the second tubular member.

7. The balloon catheter as set forth in claim 5, wherein an axial length of the tapered portion, where the outside diameter becomes smaller toward the distal end of the first tubular member, is longer than the length of the overlapped portion.

8. The balloon catheter as set forth in claims 1, 2 or 5, wherein the overlapped portion has a length of 2 mm to 50 mm.

9. The balloon catheter as set forth in claims 1, 2 or 5, wherein an axial length of the proximal end neck portion of the balloon unit is longer than the axial length of the overlapped portion.

10. The balloon catheter as set forth in claims 1, 2 or 5, wherein a proximal end opening of the guidewire lumen formed in the second tubular member is an inclined opening obtained by cutting the proximal end of the second tubular member at a slant angle.

11. The balloon catheter as set forth in claims 1, 2 or 5, wherein the first tubular member and the second tubular member are different in materials and the second tubular member is made of a material superior in flexibility compared with the first tubular member.

12. The balloon catheter as set forth in claims 1, 2 or 5, wherein said first tubular member is comprised of a material having a higher hardness than the hardness of the second tubular member.

13. The balloon catheter as set forth in claims 1, 2 or 5, wherein the first tubular member is comprised of a synthesis resin with a JIS hardness of 50D to 75D and the second tubular member is comprised of a synthesis resin with a JIS hardness of 70A to 95A.

14. The balloon catheter as set forth in claims 1, 2 or 5, wherein the second tubular member has an outside diameter smaller than an outside diameter of the first tubular member.

15. The balloon catheter as set forth in claims 1, 2 or 5, wherein said balloon unit is formed in a taper where the proximal end neck portion of the balloon unit becomes larger in inside diameter toward the proximal end.

16. The balloon catheter as set forth in claims 1, 2 or 5, wherein said first tubular member has a reinforcing wire arranged in the longitudinal direction inside said first tubular member.

17. The balloon catheter as set forth in claims 1, 2 or 5, wherein said first tubular member has a reinforcing fiber braided inside the first tubular member.

18. The balloon catheter as set forth in claims 1, 2 or 5, wherein said balloon unit is comprised of a tubular film member reduced in diameter at the two ends and the film thickness is 15 to 300 $\mu$m.

19. The balloon catheter as set forth in claims 1, 2 or 5, wherein said balloon unit has an outside diameter at the time of inflation of the balloon unit of 1.5 to 10.00 mm or so.

20. The balloon catheter as set forth in claims 1, 2 or 5, wherein said balloon unit has an axial length of the balloon unit of 15 to 50 mm.

21. The balloon catheter as set forth in claims 1, 2 or 5, wherein an axial center of the balloon unit and an axial center of the second tubular member are concentric.

* * * * *